United States Patent [19]

McGinley et al.

[11] Patent Number: 5,122,447
[45] Date of Patent: Jun. 16, 1992

[54] METHOD OF DETECTING PSEUDORABIES VIRUS SPECIFIC SERUM ANTIBODY BY USE OF A UNIVERSAL DIAGNOSTIC ANTIGEN

[75] Inventors: Michael J. McGinley; Kenneth B. Platt, both of Ames, Iowa

[73] Assignee: Iowa State University Research Foundation, Inc., Ames, Iowa

[21] Appl. No.: 299,990

[22] Filed: Jan. 23, 1989

[51] Int. Cl.⁵ .......................................... G01N 33/569
[52] U.S. Cl. ..................................... 435/5; 435/7.92; 435/235.1; 424/89
[58] Field of Search .............. 435/5, 7.92, 7.93, 235.1, 435/69.1; 436/518, 530, 531; 424/89; 530/350, 395

[56] References Cited

U.S. PATENT DOCUMENTS 4,810,634  3/1989  Post et al. ........................... 435/235

FOREIGN PATENT DOCUMENTS 0133200  2/1985  European Pat. Off. ................ 435/5
00862   2/1987  World Int. Prop. O. .............. 435/5

OTHER PUBLICATIONS

Platt, Vet. Microb. 9:35-51 (1984), The Evaluation of a Lectin-Agarose Based Subunit Vaccine and Complementary Diagnostic Antigen for Aujeszky's Disease (Pseudorabies) in the Pig.

Stevely, J. of Virol. 16:944-950 (1975), Virus-Induced Proteins in Pseudorabies-Infected Cells.

McGinley and Platt, Am. J. of Vet. Res. 50:1290-1293, Antibody Response of Pseudorabies Virus Subunit--Vaccinated Pigs to Viral Nucleocapsid Proteins Following Low-Dose Virus Challenge of Immunity, (Aug. 1989).

Van Oirschot et al., "Differentiation of Serum Antibodies from Pigs Vaccinated or Infected with Aujeszky's Disease Virus by a Competitive Enzyme Immunoassay", J. Gen. Virol. 67: 1179-1182 (1986).

Herbrink et al., "The Antigen Spot Test (AST): A Highly Sensitive Assay for Detection of Antibodies" J. Immunol. Methods 48: 293-298 (1982).

*Primary Examiner*—Esther L. Kepplinger
*Assistant Examiner*—Carol E. Bidwell
*Attorney, Agent, or Firm*—Tilton, Fallon, Lungmus & Chestnut

[57] ABSTRACT

A method of testing serum from swine vaccinated against pseudorabies virus with viral envelope-based subunit vaccines to determine the presence of antibodies to infecting pseudorabies virus in wihch an immunoassay is performed on the swine serum using a pseudorabies virus antigen preparation comprising nucleocapsid proteins of the pseudorabies virus. The universal diagnostic antigen is one or more nucleocapsid proteins having relative molecular weights of approximately 23 k, 34 k, 41 k, 63 k and 140 k.

4 Claims, 1 Drawing Sheet

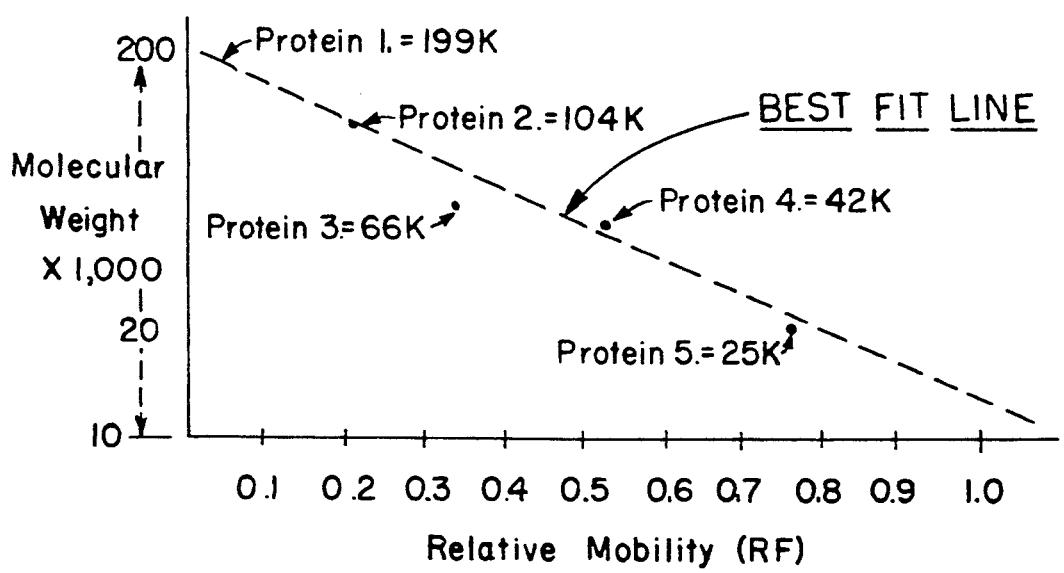

METHOD OF DETECTING PSEUDORABIES VIRUS SPECIFIC SERUM ANTIBODY BY USE OF A UNIVERSAL DIAGNOSTIC ANTIGEN

GRANT REFERENCE

The research work leading to this invention was funded in part under USDA-ARS Cooperative Agreement Number 58-6125-6-4 and USDA-SEA Special Grant No. 83-CRSR-2-2267.

FIELD OF INVENTION, BACKGROUND AND PRIOR ART

The field of this invention relates to a method of using a universal diagnostic antigen derived from pseudorabies (PR) virus or prepared by recombinant DNA techniques. More specifically, the invention relates to the use of non-enveloped structural proteins or nucleocapsid proteins as diagnostic antigens, which are complementary to the antigen of a PR enveloped subunit derived vaccine, thereby permitting PR virus carriers to be distinguished from vaccinated swine. For convenience of reference, the abbreviation "PR" is used herein to mean "pseudorabies38 .

Swine found positive in the standard assay procedure for the presence of serum antibodies to PR virus, such as the enzyme-linked immunosorbant assay (ELISA) are assumed to be actual or potential carriers of the virus. However, positive reactions may be due to recovery from natural infection and/or vaccine immunization or a combination of both, and the swine may not be carriers of the virus. Consequently, positive reactions for pigs may or may not indicate a carrier of the virus. False negative reactions are possible. However, negative pigs are considered non-carriers with the understanding that false negatives do occur occasionally.

Subunit vaccines for pseudorabies have been developed and they are prepared to contain less than the full complement of antigens from the virus and, specifically, only the glycoprotein antigens of the virus. U.S. Pat. Nos. 4,470,967 and 4,493,825 describe subunit vaccines for PR containing glycoprotein antigens. Subunit vaccines consisting of one or more viral enveloped glycoproteins should reduce losses due to clinical disease and reduce the spread of virus within and between swine herds. Further, subunit vaccinated pigs unlike pigs vaccinated with traditional vaccines can be certified free of PR by testing for antibody to viral components that are not part of a subunit vaccine. It is the ability to identify virus infected subunit vaccinated pigs that make the subunit vaccine useful in control programs.

Since not all subunit vaccines will consist of the same viral glycoprotein, veterinary diagnostic laboratories need to have access to accurate vaccination records of individual animals and also to have the capacity to test for antibodies to several different diagnostic antigens. These requirements will increase the cost of control programs but can be avoided with the use of a universal diagnostic antigen. Pseudorabies virus non-enveloped structural proteins or, more specifically, nucleocapsid proteins are logical candidates for a universal diagnostic antigen because they have not been shown to play a role in protective immunity and will most likely not be a component of subunit vaccines.

SUMMARY OF THE INVENTION

For purposes of clarification, terms should be defined. Enveloped proteins are defined as structural and nonstructural proteins that are part of the viral envelope. Non-enveloped proteins are defined as structural and non-structural proteins not associated with the viral envelope. Non-enveloped structural proteins are defined as structural proteins of the nucleocapsid. Nucleocapsid proteins are defined as non-structural and structural proteins that are associated with the nucleocapsid.

The non-enveloped structural proteins or, more specifically, the nucleocapsid proteins used in the method of this invention can be detected by SDS-PAGE analysis. The Western immunoblot assay is similar to SDS-PAGE and is used for detecting antibodies to the nucleocapsid proteins. Molecular weights for the nucleocapsid proteins can be determined by the method described in Stevely, *J. Virol.*, Vol., 16, No. 5, p. 944–950 (October, 1975). The method involves the measurement of molecular weights of the viral proteins calculated from their migration on acrylamide gels relative to that of standard proteins. The molecular weight or relative molecular mass $M_r$, is the ratio of the mass of a molecule to one-twelfth of the mass of carbon 12.

According to the present invention, five nucleocapsid proteins have been identified that can be used to detect virus infection in pigs vaccinated with viral envelope-based subunit vaccines. These five nucleocapsid proteins have molecular weights of 140k, 63k, 41k, 34k and 23k. Combinations of these may also be used to provide reliable detection of nucleocapsid specific antibody response. These proteins are useful as universal diagnostic antigens in direct and competitive enzyme-linked immunosorbant assays.

DESCRIPTION OF THE DRAWINGS

FIG. 1 describes the relative mobility (RF) of molecular weight standards which are used to construct a standard curve by best fit line/linear regression analysis.

DETAILED DESCRIPTION

The present invention relates to a method of testing serum from swine vaccinated against pseudorabies virus with viral envelope-based subunit vaccines to determine the presence of antibodies to infecting pseudorabies virus in which an immunoassay is performed on the swine serum using a pseudorabies virus antigen preparation comprising non-enveloped proteins of the pseudorabies virus, specifically, the nucleocapsid proteins.

The nucleocapsid proteins, i.e., diagnostic universal antigens, used in the method of this invention can be produced and isolated using a modification of the method described by Gibson and Roizman (*J. Virol.*, 1044–1052, 1972) for the isolation of herpes simplex type I and II nucleocapsids.

For example, a standard roller bottle apparatus may be used. A cell line is selected, such as kidney cells adapted for in vitro propagation, the cells being ones in which PR virus replicates freely. The cells are introduced into the roller bottles together with a suitable cell growth medium. Virus infected cells are harvested 24 hours later with the aid of glass beads and pelleted by low speed centrifugation. The cell pellets are washed three times in 500 mM NaCl, 20 mM Tris, pH 7.5 (TBS), resuspended in cell lysis buffer (150 mM NaCl, 10 mM Tris, 2 mM MgCl, pH 7.5) and incubated for 30 minutes at 0° C. according to usual practice. Infected cell nuclei containing non-enveloped virus are released from the cell and isolated by low speed centrifugation, washed twice in cell lysis buffer and subsequently lysed in nuclei disruption buffer consisting of 5% sodium deoxycholate in cell lysis buffer. The lysate is then incubated according to usual practice in the presence of 50 µg/ml DNase I (Sigma Chemical, St. Louis, Mo.) and clarified by low-speed centrifugation. The clarified supernatant is layered into a 5% to 45% glycerol step gradient. Nucleocapsids are pelleted by centrifugation and resuspended in TBS containing 10 mM of the protease inhibitor phenylmethylsulfonyl flouride (Sigma Chemical, St. Louis, Mo.). Resuspended nucleocapsids are absorbed for 30 minutes at room temperature with *Lens culinaris* agglutinin covalently linked to agarose beads to remove any residual PR glycoproteins that may be present. The nucleocapsid preparation is aliquoted and stored at −70° C. until used.

The proteins utilized in the assay of the present invention may also be prepared by recombinant DNA technology using the baculovirus expression system. Typically, a complementary DNA (cDNA) expression library is formed with lambda bacteriophage (gtll) which is screened with rabbit anti-nucleocapsid immunoglobulin. The specific cDNA encoding each nucleocapsid protein is cloned into a baculovirus transfer vector which is used to insert the cDNA into the polyhedrin gene of the *Autographic californica* nuclear polyhedrosis virus, A$_c$MNPV, resulting in the creation of a recombinant baculovirus. The specific nucleocapsid proteins can be produced in *Spodoptera frugiperda* or any other suitable cells that are infected with recombinant virus resulting in the production of large quantities of the proteins. The recombinant nucleocapsid protein can be used in a standard immunoassay, such as the enzyme-linked immunosorbant assay, for its ability to detect homologous antibody in virus infected subunit vaccinated and non-vaccinated pigs.

More specifically, the production of recombinant PR virus nucleocapsid antigens using the baculovirus expression vector system can be accomplished in eight general steps:

1. Identification of immunogenic nucleocapsid antigen candidates and generation of PR virus nucleocapsid specific monoclonal antibody and polyclonal hyperimmune serum. (23k, 34k, 41k, 63k and 140k relative molecular weights.

2. Isolation of mRNA present in PR virus infected cells 6-9 hours post inoculation (period when the PR virus structural component genes, encoding enveloped glycoproteins and nucleocapsid proteins, are transcribed) and synthesis of complementary DNA (cDNA) from these mRNA.

3. Construction of a lambda bacteriophage (gtll) library using PR virus derived cDNA.

4. Screening of clones obtained from step (3) using PR nucleocapsid specific hyperimmune serum to identify and isolate lambda gtll bacteriophage containing nucleocapsid genes.

5. Excision of the putative nucleocapsid genes from gtll bacteriophage followed by ligation into specially designed baculovirus plasmid transfer vectors.

6. Transfection of permissive insect cell culture with the transfer vector containing the putative nucleocapsid gene and infectious baculovirus DNA.

7. Identification and isolation of recombinant baculovirus expressing PR virus nucleocapsid genes using one or more of the following techniques: plaque phenotype, SDS-PAGE protein profile, antibody probing of plaques, or radioimmunoprecipitation of recombinant baculovirus using nucleocapsid specific antibody.

8. Expansion of confirmed PR virus nucleocapsid/baculovirus recombinants in insect tissue culture and isolation of nucleocapsid antigens either expressed and secreted or incorporated into the baculovirus.

The PR virus nucleocapsid proteins of the present invention can be characterized by molecular weight determination. For example, the isolated non-enveloped PR virions can be electrophorectically separated to resolve individual nucleocapsid proteins under reducing conditions using standard SDS-PAGE methodology according to B.D. Hames, *Gel Electrophoresis of Proteins: A Practical Approach*, Chapter 1, IRL Press, Washington, D.C. (1985). Further, commercially prepared molecular weight standard proteins from Sigma Chemical Co., St. Louis, Mo., are separated according the same methodology to allow molecular weight estimates on individual PR virus nucleocapsid proteins. The resolved nucleocapsid proteins and molecular weight standards are then electrophoretically transferred to nitrocellulose paper using the Western immunoblot assay. A manufacturer of Western immunoblot transfer apparatus is Bio-Rad, Inc., Richmond, Calif.

Following separation and transfer, the molecular weight standards are cut from the nitrocellulose sheet and stained for total protein according to known procedures. Hancock, et al., *Anal. Biochem.*, 133:157–162 (1983). Typically, the procedure allows the investigator to visualize and make migration measurements on individual molecular weight standard proteins. The relative mobility (Rf) of the molecular weight standards and their reported molecular weights are used to construct a standard curve by best-fit line/linear regression analysis. The standard curve is used to estimate the molecular weight of the nucleocapsid proteins using their respective Rf values on a standard curve generated as described. FIG. 1 describes the values plotted on semi-log paper and the best-fit line is made. The proteins identified for use in the present invention include those having molecular weights of 140k, 63k, 41k, 34k and 23k. These proteins have been found to be effective in the present invention when used singly or in combination.

The nucleocapsid proteins described above can be used in conventional standard immunoassay procedures, for example—any assay where the swine serum and selected nucleocapoid antigen may be combined and prepared for a time and under conditions sufficient for formation of immune complexes between the antibody in the serum and the antigen and detecting the presence of immune complexes. Some of these assays include the competitive and indirect enzyme-linked immunosorbant assay (ELISA) procedure, described in van Oirshot, et al., *J. Gen. Virol.*, 67:1179-1182 (1986) and McGinley and Platt, *Am. J. Vet. Res.*, 49:1489-1493 (1988), respectively; the immunoblot assay, described in McGinley and Platt, *Am. J. Vet. Res.*, 1989, (accepted for publication) and in Towbin and Gordon, *J. Immunol. Meth.*, 72:313-340 (1985); the agglutination assay using latex particles, described in Weissfield and Sonenworth, *J. Clin. Microbiol.*, 16:971-972 (1982); the radial immunodiffusion enzyme assay, described in Joo, et al., *Am J. Vet. Res.*, 45:2096-3098 (1984); the radioimmunoassay, described in Yalow, *Textbook of Endocrinology*, ed. Williams, pp. 123-132, the indirect hemagglutination assay as described in Bernstein and Stewart, *Appl. Microbiol.*, 21:84-89 (1971), the microimmunodiffusion assay, described in Ouchterlony, *Acta Pathol. Microbiol. Scand.*, 25:186-191 (1948), and others.

All of these assays include a step in which the selected protein antigen is exposed to the serum sample for selective binding reaction with antibodies in the serum which have been generated to the same protein antigen, for example, by pseudorabies viral replication in the pig from which a serum specimen is obtained.

The method of this invention and the preparation of the nucleocapsid proteins utilized therein is further illustrated by the following experimental examples:

EXAMPLE 1

PR Virus Nucleocapsid Antigen Preparation

PR virus nucleocapsids were produced and isolated using a modification of the method described by Gibson and Roizman for isolation of herpes simplex type I and II by nucleocapsids. *J. Virol.*, 10:1044-1052 (1972). Cell monolayers are prepared in plastic roller bottles. The cell type used is Madin Darby bovine kidney cells (National Veterinary Services Laboratory, Ames, Iowa). Other cell types that support the replication of pseudorabies virus may also be used. The cell monolayers are inoculated with pseudorabies virus strain Be (Platt, et al., *Arch Virol.* 60:13-23 (1979)) at a multiplicity of infection of 5.0 and incubated at a temperature of 37° C. The cells were harvested 24 hours later with the aid of glass beads and pelleted by low speed centrifugation at $1,000 \times$ g for 15 minutes. The cell pellets were washed three times in 500 m NaCl, 20 mM Tris, pH 7.5 (TBS), resuspended in 20 ml of cell lysis (CL) buffer consisting of 150 mM NaCl, 10 mM Tris, 2 mM $MgCl_2$, pH 7.5, containing 1% Nonidet P-40 and incubated for 30 minutes at 0° C. Infected cell nuclei were isolated by low speed centrifugation, washed twice in CL buffer and lysed in nuclei disruption buffer consisting of 5% sodium deoxycholate in CL buffer. The lysate was incubated at 37° C. for one hour in the presence of 50 µg/ml DNase I and clarified by low speed centrifugation. The clarified supernatant was layered onto a 5% to 45% glycerol step gradient. Nucleocapsids were pelleted by centrifugation at 24,000 rpm for 90 minutes and resuspended in TBS containing 10mM of the protease inhibitor phenylmethylsulfonyl fluoride. Resuspended nucleocapsids were adsorbed for 30 minutes at room temperature with *Lens culinaris* agglutinin covalently linked to agarose beads to remove any residual PR virus glycoproteins that might be present. The nucleocapsid preparation was aliquoted and stored at −70° C. *Sodium Dodecyl Sulfate-Polyacrylamide Gel Electrophoresis (SDS-PAGE)*.

PR virus nucleocapsid protein and molecular weight markers were diluted in an equal volume of sample preparation buffer consisting of 2% SDS, β-mercaptoethanol, 0.05% bromophenol blue and 50% glycerol in 0.5M Tris buffer, pH 6.8, boiled for 5 minutes and separated under reducing conditions by standard SDS-PAGE methods. Stacking and separating gels consisted of 4% and 10% acrylamide monomer respectively, cross-linked with bis-acrylamide at a ratio of 30:0.8. All gels were electrophoresed at 25 mA until the samples reached the stacking gel/separating gel interface. Sample separation was completed by electrophoresis at a constant current of 35 mA until the dye front had migrated 15 cm. The 15 cm migration limit was imposed on all separations in an attempt to standardize protein migration patterns for later molecular weight determinations and comparisons.

Electrophoretic Transfer of PR Virus Proteins

PR virus nucleocapsid protein and pre-stained molecular weight standards were electrophoretically transferred to nitrocollulose membranes immediately following SDS-PAGE. Proteins were transferred for 16 hours at 30 V followed by a two hour finishing period at 100 V in transfer buffer consisting of 25 mM Tris, 192 mM glycine, pH 8.3 and 20% v/v methanol. Following transfer, the nitrocellulose membranes were cut into 0.5 cm strips, air dried, and used immediately. The efficiency of transfer and total protein profile was evaluated by india ink total protein staining.

Western Immunoblot Assay

Nitrocellulose strips containing separated nucleocapsid protein were blocked with 2.5% gelatin in TBS for two hours at 37° C. and were washed for three 5-minute cycles in TBS containing 0.05% Tween (20) TTBS). Positive control, negative control and sample sera were diluted 1/100 in TTBS containing 1% gelatin, incubated with the nitrocelluose strips for one hour at room temperature, and washed as described above. Specific antigen-antibody reactions were visualized with biotin labeled goat anti-porcine IgG (H+L) secondary antibody diluted 1/2000 and streptavidin-horseradish peroxidase conjugate diluted 1/4000. All incubations were for one hour at room temperature with washing as described above. Enzyme substrate was prepared immediately before use and consisted of 60 mg of 4-chloro-1-napthol in 20 ml of ice cold methanol and 60 µl of cold 30% hydrogen peroxide in 100 ml of TBS. Color reactions were developed at room temperature in the dark for 40 minutes and stopped by two brief washes in deionized water. Non-specific reactions were identified by incubating nucleocapsid protein nitrocellulose strips with TTBS containing 1% gelatin in place of serum. The reported molecular weights represent a minimum of three independent measurements.

EXAMPLE 2

PR Virus Subunit Vaccine Preparation

The vaccine can be prepared by conventional means, such as that described by Platt, et al., *Vet. Microbiol.*, 11:25–40 (1986). Essentially, viral glycoproteins were extracted from detergent solubilized PR virus infected porcine kidney 1a cells (Veterinary Medical Research Institute, Iowa State University, Ames, Iowa) isolated by lectin affinity chromatography using *Lens culinaris* agglutinin covalently linked to agarose beads (E-Y Laboratories, San Mateo, Calif.). Bound glycoprotein was eluted with 2.5% mannose in 0.025M Tris/Tricine, pH 8.4 and concentrated 10-fold by ultra-filtration through a membrane (Amacon Corp., Danvers, Mass.) with a 30,000 molecular weight cut-off limit. The protein concentration of the column eluate was determined by a dye binding method described by Bradford, *Anal. Biochem.*, 72:248-252 (1976). Vaccine antigen was diluted in Tris/Tricine and emulsified in an equal volume of Freund's incomplete adjuvant.

EXAMPLE 3

Ten pigs were inoculated subcutaneously with one 100 µg and two 50 µg doses of viral glycoprotein vaccine antigen, as described in Example 2, at three-week intervals. Vaccinates and six non-vaccinated controls were nasally challenged with $10^{2.3}$ PFU of PR virus in 2 ml of maintenance medium, 21 days after the third vaccine dose. Serums were collected on days 0, 4, 7, 10, 14, and 21 post challenge and assayed for serum neutralization and nucleocapsid specific antibody. The control pigs were terminated at this time. Challenged vaccinates were maintained through day 113 post-challenge and the antibody response of these pigs to individual nucleocapsid protein was characterized by the Western immunoblot assay. Specific antibody responses to individual proteins are shown in Tables I and II:

TABLE I

The collective antibody response of 10 subunit vaccinated pigs to nucleocapsid protein (NCP) as detected by Western immunoblot assay.

| NCP | Day Tested Post-Challenge | | | | | | | | |
|---|---|---|---|---|---|---|---|---|---|
|     | 0 | 7 | 10 | 14 | 21 | 32 | 53 | 96 | 113 |
| 140k | 0[a] | 0 | 0 | 8 | 8 | 8 | 7 | 6 | 4 |
| 63k | 0 | 0 | 0 | 9 | 9 | 9 | 7 | 5 | 5 |
| 41k | 0 | 0 | 0 | 10 | 10 | 10 | 9 | 9 | 7 |
| 34k | 0 | 0 | 0 | 10 | 10 | 10 | 8 | 6 | 6 |
| 23k | 0 | 0 | 0 | 8 | 8 | 8 | 8 | 8 | 8 |

[a]Total number of pigs with detectable antibody to nucleocapsid protein.

TABLE II

The individual antibody response of 10 subunit vaccinated pigs to five nucleocapsid proteins (NCP) as detected by Western immunoblot assay on day 113 post-challenge.

| Pig No. | 140k | 63k | 41k | 34k | 23k |
|---|---|---|---|---|---|
| 1 | +[a] | + | −[b] | + | + |
| 2 | + | + | + | − | − |
| 3 | − | − | + | − | + |
| 4 | − | − | − | − | − |
| 5 | − | − | + | + | + |
| 6 | − | − | + | + | + |
| 7 | + | + | + | − | + |
| 8 | − | − | + | + | + |
| 9 | + | + | + | + | + |
| 10 | − | + | − | + | + |

[a](+) = NCP-specific antibody detected
[b](−) = NCP-specific antibody not detected Subunit-vaccinated pigs became non-clinically infected with PR virus following nasal challenge as indicated by a four to eight fold increase in individual serum neutralization antibody titers to maximum levels which occurred at day 21 post-challenge. The serum neutralization procedure is described by Platt, et al., *Vet. Microbiol.*, 11:25–40 (1986). The serum neutralization titers of individual pigs steadily declined thereafter through day 113 post-challenge indicating that periods of viral recrudesence did not occur. Non-immunized control pigs survived virus challenge but became depressed, stopped eating, lost weight and developed respiratory congestion. These pigs were killed on day 21 post-challenge.

A representative antibody response of subunit-vaccinated, 21 days post-challenge antibody response (B) and non-immunized control (A) pigs to nucleocapsid proteins as detected by the Western immunoblot assay following virus challenge was determined. Antibody to a total of eight proteins was detected. However, only five nucleocapsid proteins with molecular weights of 140k, 63k, 41k, 34k and 23k were consistently detected with PR virus specific antibody. The three remaining nucleocapsid proteins with molecular weights of 120k, 82k and 26k were not consistently detected with specific antibody. Two additional bands represented proteins with molecular weights of 56k and 30k that consistently reacted non-specifically with the biotin/streptavidin conjugate following incubation with buffer alone.

In Table I, it is noted that no antibody to PR virus nucleocapsid proteins was detected in 10 immunized pigs prior to virus challenge. Antibody to each of the five nucleocapsid proteins was first detected on day 14 post-challenge in immunized and non-immunized pigs. The most immunogenic of the five nucleocapsid proteins were the 23k, 34k and 41k proteins based on the number of pigs that produced antibodies to these proteins throughout the 113 day test period. Antibody to these three nucleocapsid proteins was initially detected in eight, ten and ten pigs, respectively, and continued to be detected through day 113 post-challenge in eight, six and seven pigs, respectively. See Tables I and II.

EXAMPLE 4

Indirect Enzyme-Linked Immunosorbant Assay (ELISA)

Individual or combinations of nucleocapsid protein are used in the indirect enzyme-linked immunosorbant assay (ELISA) for the detection of PR virus specific antibodies. The test is performed by diluting nucleocapsid protein in antigen coating buffer consisting of 0.02 M sodium carbonate/bicarbonate buffer pH 9.6 containing 1 mg/ml of water soluble carbodiimide 1-ethyl-3-(-3-dimethylaminopropyl) carbodiimide (Sigma Chemical Company, St. Louis, Mo.) to enhance antigen binding. One hundred $\mu$l of antigen preparation is incubated at 4° C. for 16–24 hours in individual wells of polystyrene microplates (Immunlon I microplates, Dynatech Labs, Inc., Alexandria, Va.). Unadsorbed antigen is removed by washing all wells three times with 0.01M phosphate buffered saline, pH 7.2 containing 0.5% Tween 20 (ELISA wash buffer). Unreacted sites are blocked by treating individual wells with 2.0% gelatin in antigen coating buffer for two hours at 37° C. Serums to be tested are diluted 1/20 in antibody/conjugate diluent consisting of 0.5M Tris, 150 mM sodium chloride, 0.01 mM EDTA, pH 7.4 containing 0.5% Tween and 1.0% gelatin. Diluted serums are added at a rate of 100 $\mu$l to individual nucleocapsid protein coated wells and to control wells coated with 2% gelatin. Diluted serums are incubated at 37° C. for 15 minutes, washed eight times with ELISA wash buffer and air dried for 10 minutes. Goat anti-porcine IgG (H+L) conjugated to horseradish peroxidase (Kirkegaard & Perry Laboratories, Inc., Gaithersburg, Md.) is diluted 1/3500 in antibody/conjugate diluent, added at a rate of 100 $\mu$l well and incubated at 37° C. for 45 minutes. Plates are washed eight times with ELISA wash buffer as described above. One hundred $\mu$l of enzyme substrate is prepared by adding 50 $\mu$l of a 30% concentrated solution of hydrogen peroxide and 20 mg of o-phenylenediamine chromagen to 100 ml of 0.02M citric acid, pH 5.0, and added to individual wells and reacted in the dark at 25° C. for 20 minutes. The resulting color reactions are stabilized with 4.5M sulfuric acid. Absorbance values are determined with an automatic microplate reader (Dynatech MR600 microplate reader, Dynatech Labs, Inc.) equipped with a test filter wavelength of 490 nm. Absorbance values of individual samples are determined by subtracting the optical density value of control wells from the optical density value of nucleocapsid protein coated wells and expressed as the mean of four replications. A baseline optical density reaction is established with 40 known negative serums that give a corrected optical density range of 0.000 to 0.050. Corrected optical density values of 0.150 or greater are considered positive. Mean corrected optical density values of 0.051 to 0.149 are considered suspicious. Values equal to or less than 0.150 are considered negative.

EXAMPLE 5

Competitive Enzyme-Linked Immunosorbant Assay (ELISA)

Individual or combinations of nucleocapsid protein are also used in the competitive ELISA. Individual wells of microtiter plates are coated with nucleocapsid protein and/or gelatin as described in Example 4. Alternatively, nucleocapsid protein can be bound to wells by antibody-antigen capture using nucleocapsid protein specific mouse monoclonal antibodies. Swine serums to be tested are diluted 1:20 in antibody/conjugate diluent. Diluted serums are added at a rate of 100 µl to individual nucleocapsid protein coated wells and gelatin coated control wells. Microtiter plates are incubated at 37° C. for 45 minutes, washed eight times with ELISA wash buffer and air dried for 10 minutes. An optimum dilution of goat anti-nucleocapsid protein specific polyclonal or mouse monoclonal antibodies conjugated to horse radish perioxidase is added at a rate of 100 µl to individual test and control wells. Microtiter plates are incubated at 37° C. for 45 minutes and washed as above. Enzyme substrate is added to individual wells, color reactions are allowed to develop and are stabilized as described in Example 4. Absorbance values are determined as described in Example 4. Corrected optical density values of 0.150 an greater are negative. Values between 0.149 and 0.075 are suspicious and values less than 0.075 are considered positive.

Pigs immunized with viral envelope protein and subsequently exposed to a low dose of virus will produce detectable antibodies to at least five nucleocapsid proteins with molecular weights of 140k, 63k, 41k, 34k and 23k. The 23k, 34 k and 41 k proteins were the most immuogenic based on the amount of time that specific antibodies could be detected in individual pigs. Further, nine of ten vaccinated pigs had detectable antibodies to one or more of these proteins at any time during the 113 day test period. Consequently, these nucleocapsid proteins are useful as a universal diagnostic antigen in indirect and competitive enzyme-linked immunoassays.

Upon reviewing the results of the Western immunoblot assay and the following examples, it may be argued that the assay was able to detect antibody to nucleocapsid protein following a low dose virus exposure because the pigs were sensitized with nucleocapsid protein that may have been present in the immunizing preparation. This possibility is considered unlikely because antibody to nucleocapsid protein was first detected on day 14 post-challenge in both immunized and non-immunized control pigs. Failure to detect antibody to nucleocapsid protein earlier in immunized pigs and in control pigs indicates that the presence of nucleocapsid protein specific antibody was a result of a primary immune response.

EXAMPLE 6

Dot Immuno-Blot Assay Using PrV Nucleocapsid Antigen

The following example involves the detection of nucleocapsid specific antibody using a procedure similar to the indirect ELISA technique. The difference in this application is that antigen is bound to, and antibody reactions take place on a membrane solid support such as nitrocellulose.

The following procedure requires that a vacuum filtration apparatus be used. One such apparatus is the Bio-Dot microfiltration apparatus (Bio-Rad Laboratories). A nitrocellulose membrane cut to fit the apparatus is thoroughly wetted in 20 mM Tris, 500 mM NaCl, pH 7.5 (TBS). The wetted membrane and vacuum filtration apparatus are assembled as per manufacturer's instructions. One hundred µl of an antigen solution containing the nucleocapsid protein(s) diluted in TBS is added to all wells of the Bio-Dot apparatus and allowed to bind to the nitrocellulose by gravity flow (approximately 30-40 minutes). After the antigen solution has completely drained from the wells, 200 µl of blocking solution (TBS+0.05% Tween 20 and 2% gelatin) is added to all wells and allowed to gravity flow through the membrane (approximately 60 minutes). Following completion of blocking, 300 µl of TTBS wash solution (TBS+0.05% Tween 20) is added to all wells and drawn through using a slight vacuum. This wash step is repeated a minimum of three times.

A membrane prepared in the above manner can now be probed with serum from a pig immunized with a PrV envelope glycoprotein(s) subunit vaccine for reactivity with nucleocapsid antigen. The antibody probing would proceed as follows: sample pig sera would be diluted (typically 1:20 to 1:100) in antibody buffer (TTBS+1% gelatin) and 100 µl of each diluted sample applied to the appropriate sample well. The antibody solution (termed first antibody) is allowed to react with the bound nucleocapsid antigen by gravity filtration (30-40 minutes). Following the first antibody reaction, the membrane is washed three times (300 µl per wash) with TTBS as previously described. Following removal of excess wash solution by vacuum application, 100 µl of diluted (typically 1:1000 to 1:3000) goat anti-pig IgG conjugated with horseradish peroxidase (termed 2nd antibody-HRP) is added and allowed to react by gravity filtration as previously described. The membrane is washed three times with TTBS as described above followed by three washes in TBS prior to color development.

The presence of specific anti-nucleocapsid antibody in the pig serum sample is now visualized by color development of the nucleocapsid-1st antibody-2nd antibody-HRP complex that is bound to the membrane. Two hundred µl of color development solution (60 mg 4-chloro-1-napthol, 60 µl of cold 30% hydrogen peroxide, and 20 ml of cold methanol in 100 ml of TBS) is added to each well and allowed to react for 30 minutes at room temperature in the dark. The deposition of a purple precipitate (dot) indicates the presence of specific anti-nucleocapsid antibody. As in all assays of this type, appropriate known positive and known negative serum samples are included to gauge the reactivity of unknown serum samples.

What is claimed is:

1. The method of testing serum from a swine vaccinated against pseudorabies virus with a viral pseudorabies envelope-based glycoprotein subunit vaccine to determine the presence of antibodies to infecting pseudorabies virus, comprising performing an immunoassay on a swine serum specimen from said vaccinated animal by contacting the specimen with a protein reagent selected from the group consisting of pseudorabies nucleocapsid proteins having relative molecular weights of approximately 23kD, 34kD and 41kD, or mixtures of said proteins, and determining is serum antibodies have bound to said protein reagent, antibody binding indicating that the vaccinated animal has been infected by pseudorabies virus.

2. The method of claim 1 in which said protein reagent is the pseudorabies nucleocapsid protein having a relative molecular weight of approximately 23kD.

3. The method of claim 1 in which said protein reagent is the pseudorabies nucleocapsid protein having a relative molecular weight of approximately 34kD.

4. The method of claim 1 in which said protein reagent is the pseudorabies nucleocapsid protein having a relative molecular weight of approximately 41kD.

* * * * *

UNITED STATES PATENT AND TRADEMARK OFFICE
CERTIFICATE OF CORRECTION

PATENT NO. : 5,122,447
DATED : June 16, 1992
INVENTOR(S) : McGinley et al.

It is certified that error appears in the above-identified patent and that said Letters Patent is hereby corrected as shown below:

Column 11, line 11, delete "is" and substitute --if--.

Signed and Sealed this

Fourteenth Day of September, 1993

Attest:

BRUCE LEHMAN

Attesting Officer     Commissioner of Patents and Trademarks